United States Patent
Liu et al.

(10) Patent No.: US 12,183,017 B2
(45) Date of Patent: Dec. 31, 2024

(54) CAPSULE ENDOSCOPE IMAGE THREE-DIMENSIONAL RECONSTRUCTION METHOD, ELECTRONIC DEVICE, AND READABLE STORAGE MEDIUM

(71) Applicant: ANKON TECHNOLOGIES CO., LTD, Wuhan (CN)

(72) Inventors: Hui Liu, Wuhan (CN); Wenjin Yuan, Wuhan (CN); Hang Zhang, Wuhan (CN); Hao Zhang, Wuhan (CN)

(73) Assignees: ANKON TECHNOLOGIES CO., LTD., Wuhan (CN); ANX ANX IP HOLDING PTE. LTD., Singapore (SG)

( * ) Notice: Subject to any disclaimer, the term of this patent is extended or adjusted under 35 U.S.C. 154(b) by 41 days.

(21) Appl. No.: 18/268,239

(22) PCT Filed: Nov. 23, 2021

(86) PCT No.: PCT/CN2021/132433
§ 371 (c)(1),
(2) Date: Jun. 18, 2023

(87) PCT Pub. No.: WO2022/127533
PCT Pub. Date: Jun. 23, 2022

(65) Prior Publication Data
US 2024/0054662 A1 Feb. 15, 2024

(30) Foreign Application Priority Data
Dec. 18, 2020 (CN) .......................... 202011499202.7

(51) Int. Cl.
*G06T 7/593* (2017.01)
*A61B 1/00* (2006.01)
(Continued)

(52) U.S. Cl.
CPC .......... *G06T 7/337* (2017.01); *A61B 1/00009* (2013.01); *A61B 1/041* (2013.01);
(Continued)

(58) Field of Classification Search
CPC ......... G06T 7/337; G06T 7/85; G06T 7/0014; G06T 2207/10012; G06T 2207/10068;
(Continued)

(56) References Cited

U.S. PATENT DOCUMENTS

2020/0082510 A1   3/2020   Wang et al.
2020/0128225 A1   4/2020   Ge et al.

FOREIGN PATENT DOCUMENTS

CN   109377530 A   2/2019
CN   110033465 A   7/2019
(Continued)

*Primary Examiner* — Ayman A Abaza
(74) *Attorney, Agent, or Firm* — Treasure IP group, LLC

(57) ABSTRACT

A method of three-dimensional reconstruction of capsule endoscope images is described. The method combines two algorithms for obtaining image depth information values to improve the calculation accuracy of image depth values, and thus to increase the image three-dimensional reconstruction rate and improve the image identification precision.

9 Claims, 3 Drawing Sheets

(51) Int. Cl.
    *A61B 1/04*     (2006.01)
    *G06T 7/00*     (2017.01)
    *G06T 7/33*     (2017.01)
    *G06T 7/80*     (2017.01)

(52) U.S. Cl.
    CPC ............ *G06T 7/0014* (2013.01); *G06T 7/593* (2017.01); *G06T 7/85* (2017.01); *G06T 2207/10012* (2013.01); *G06T 2207/10068* (2013.01); *G06T 2207/30028* (2013.01); *G06T 2207/30096* (2013.01)

(58) Field of Classification Search
    CPC . G06T 2207/30028; G06T 2207/30096; A61B 1/00009; A61B 1/041
    USPC .......................................................... 348/45
    See application file for complete search history.

(56) References Cited

FOREIGN PATENT DOCUMENTS

| | | | | |
|---|---|---|---|---|
| CN | 110335318 A | | 10/2019 | |
| CN | 110992431 A | * | 4/2020 | ............. G06T 17/00 |
| CN | 111210468 A | | 5/2020 | |
| CN | 111524071 A | | 8/2020 | |

\* cited by examiner

CAPSULE ENDOSCOPE IMAGE THREE-DIMENSIONAL RECONSTRUCTION METHOD, ELECTRONIC DEVICE, AND READABLE STORAGE MEDIUM

CROSS-REFERENCE OF RELATED APPLICATIONS

The application is a National Phase Application of PCT International Application No. PCT/CN2021/132433, International Filing Date Nov. 23, 2021, published Jun. 23, 2022 as International Publication Number WO2022/127533A1, which claims priority from Chinese Patent Application No. 202011499202.7, filed Dec. 18, 2020, all of which are incorporated herein by reference in their entirety.

FIELD OF INVENTION

The present invention relates to the field of medical imaging equipment, and more particularly to a three-dimensional reconstruction method of capsule endoscope images, an electronic device, and a readable storage medium.

BACKGROUND

A gastrointestinal endoscope is a medical device that integrates core components such as a camera and a wireless transmission antenna. It captures images inside the digestive tract and synchronously transmits the images to the outside for medical examination based on data of the obtained images.

The images captured by the gastrointestinal endoscope often have limited field of view due to their unique capture environment, making it difficult to identify the location, shape, and volume size of lesions based on a single two-dimensional image during use.

In order to solve above problems, in the prior art, a monocular vision system is widely used due to its simple structure and convenient application, specifically, the most classic method is a three-dimensional reconstruction of monocular vision based on the shading restoration. The monocular vision system continuously captures images through a single camera, and then, restores parameters such as the relative depth and plane direction of each point on the surface through the brightness information of the object surface in a single image.

However, for actual images, especially those captured by a capsule endoscope in the digestive tract, the brightness of the surface point image is affected by many factors such as liquid reflections and projected shadows. Therefore, three-dimensional structure reconstruction using a monocular vision system is often difficult to meet the requirements, and the measurement of lesion size also has a significant error.

By simulating the function of the human eye, a binocular stereo vision system captures two synchronized images with left and right cameras, and uses the stereo image matching and parallax to calculate the depth information of feature points in the images to complete the three-dimensional reconstruction of the images. Compared with monocular vision, the calculation results from the binocular vision system are more accurate, allowing for three-dimensional reconstruction of all images within a scene. However, for the images in the digestive tract captured by the capsule endoscope, it is difficult to extract feature points, which introduces significant errors during the stereo matching and calculation process, leading to unsatisfactory three-dimensional reconstruction results.

SUMMARY OF THE INVENTION

In order to solve above technical problems, the object of the present invention is to provide a three-dimensional reconstruction method of capsule endoscope images, an electronic device, and a readable storage medium.

In order to achieve one of above-mentioned objects of the present invention, an embodiment of the present invention provides a three-dimensional reconstruction method of a capsule endoscope image, the method comprising: obtaining a first image and a second image synchronously through two cameras arranged side by side;

matching the first image with the second image to obtain corresponding stable homonymy points, wherein the stable homonymy points are two pixels with a unique matching relationship in the first image and the second image after being processed by the same rule;

calculating a first depth information value corresponding to each pair of the stable homonymy points;

calculating a second depth information value corresponding to each pixel in a comparison image that is one of the first image and the second image;

obtaining a unique depth information value corresponding to each pixel in the comparison image based on the first depth information value and the second depth information value matched by each stable homonymy point; and obtaining a three-dimensional spatial coordinate point of each pixel in the comparison image mapped to the camera coordinate system based on the unique depth information value, and mapping the attributes of each pixel in the comparison image to the corresponding three-dimensional spatial coordinate point to complete the three-dimensional image reconstruction.

In an embodiment of the present invention, matching the first image with the second image to obtain corresponding stable homonymy points comprises:

detecting feature points using a non-rigid dense matching method, and the detected feature points are used as the stable homonymy points.

In an embodiment of the present invention, calculating the first depth information value corresponding to each pair of the stable homonymy points comprises:

obtaining a baseline distance B between two cameras, a focal length value f of the cameras relative to the imaging plane, and the coordinate values (xm1, ym1) and (xn1, yn1) of the two pixels with a unique matching relationship in each stable homologous points in the corresponding image;

the first depth information value depth (xm1, ym1) is represented as:

$$\text{depth}(xm1, ym1) = \frac{B \times f}{|xm1 - xn1|}.$$

In an embodiment of the present invention, obtaining the unique depth information value corresponding to each pixel in the comparison image based on the first depth information value and the second depth information value matched by each stable homonymy point comprises:

obtaining the first depth information value and the second depth information value that mutually matching based on the pixels in the comparison images corresponding to the stable homonymy points, and obtaining the depth residual between the first depth information value and the second depth information value;

then, d(xm1, ym1)=|depth(xm1, ym1)−depth(xm2, ym2)|;

wherein, (xm1, ym1) represents the pixel coordinate value in the comparison image corresponding to any stable homonymy point; d(xm1, ym1) represents the depth residual corresponding to the stable homonymy point with the coordinate value (xm1, ym1) in the comparison image, depth(xm1, ym1) represents the first depth information value corresponding to the stable homonymy point with the coordinate value (xm1, ym1) in the comparison image, and depth(xm2, ym2) represents the second depth information value corresponding to the stable homonymy point with the coordinate value (xm1, ym1) in the comparison image;

performing interpolation calculation based on the obtained depth residual of each stable homonymy point, to obtain the depth residuals of all pixels in the comparison image;

obtaining the unique depth information value corresponding to each pixel in the comparison image based on the depth residual of each pixel in the comparison image and the corresponding second depth information value;

then, Z(xm, ym)=depth(xm, ym)+d(xm, ym);

wherein, (xm, ym) represents the coordinate value of any pixel in the comparison image; d(xm, ym) represents the depth residual corresponding to the pixel with the coordinate value (xm, ym) in the comparison image; depth(xm, ym) represents the secondary depth information value corresponding to the pixel with the coordinate value (xm, ym) in the comparison image; and Z(xm, ym) represents the unique depth information value corresponding to the pixel with the coordinate value (xm, ym) in the comparison image.

In an embodiment of the present invention, before performing interpolation calculation based on the obtained depth residual of each stable homonymy point, the method specifically comprises:

M1, traversing the obtained depth residual d(xm1, ym1) and performing outlier analysis on it with the same parameter value to filter out obvious abnormal points; marking the stable homonymy point corresponding to the traversed depth residual value d(xm1, ym1) as an outlier and eliminating it if the traversed depth residual value d(xm1, ym1) meets the formula $$\frac{d(xm1, ym1) - \mu_d}{\sigma_d} > T;$$

wherein, $\mu_d$ represents a mean value of the depth residuals corresponding to all stable homonymy points, $\sigma_d$ represents a variance of the depth residuals corresponding to all stable homonymy points, and T is a constant;

M2, performing calculation interpolation based on the depth residuals corresponding to the remaining stable homonymy points after the elimination is completed.

In an embodiment of the present invention, after a traversing is completed in step M1, the method also comprises:

obtaining the total number a of the stable homonymy points before traversing, and the total number b of the stable homonymy points after traversing and elimination;

determining whether a is equal to b;

if a is equal to b, proceeding to step M2;

if a is not equal to b, taking the new stable homonymy points formed after elimination as the base data, and repeatedly perform step M1 until a equals b.

In an embodiment of the present invention, performing interpolation calculation based on the obtained depth residual of each obtained stable homonymy point comprises obtaining the coordinate values $(x_i, y_i)$ of P stable homonymy points in the comparison image after processing, as well as the coordinate values $(x_j, y_j)$ of Q non-stable homonymy points in the comparison image excluding the stable homonymy points, wherein the total number of pixels in the comparison image is P+Q; wherein i=1, 2 . . . P; j=1, 2 . . . Q;

calculating the distance $Dist_i(j)$ from each stable homonymy point to each non-stable homonymy point;

assigning Q weight values $W_i(j)$ to each stable homonymy point $(x_i, y_i)$ according to the value of $Dist_i(j)$;

obtaining the depth residual d(j) of each non-stable homonymy point through weighted summation;

$$Dist_i(j) = \sqrt{(x_i - x_j)^2 + (y_i - y_j)^2},$$

$$W_i(j) = \frac{1}{Dist_i(j) + e},$$

$$d(j) = \sum_{i=1}^{P} d(i) * W_i(j);$$

wherein, d(i) represents the depth residual of the stable homonymy point with serial number i, $W_i(j)$ represents the weight value for the stable homonymy point with serial number i corresponding to the non-stable homonymy point with serial number j; e is a constant value that prevents the denominator from being 0.

In an embodiment of the present invention, obtaining the three-dimensional spatial coordinates point of each pixel in the comparison image mapped to the camera coordinate system based on the unique depth information value comprises: representing the two-dimensional coordinate value of any pixel in the comparison image as (xm, ym), and representing the three-dimensional spatial coordinate of the three-dimensional spatial coordinate point formed by mapping the two-dimensional pixel (xm, ym) as (Xm, Ym, Zm)

$$Xm = \frac{f}{(xm - xo)} B,$$

$$Ym = \frac{f}{(ym - yo)} B,$$

wherein, B represents the baseline distance between two cameras, f represents the focal length value of the cameras relative to the imaging plane, (xo, yo) represents the mapping point coordinate value of the optical center of the camera forming the comparison image on the imaging plane, and the value of Zm is the unique depth information value corresponding to the two-dimensional coordinates (xm, ym).

It is another object of the present invention, in an embodiment, to provide an electronic device, comprising a memory and a processor, wherein the memory stores a computer program that runs on the processor, and the processor executes the computer program to implement the steps of the three-dimensional reconstruction method of a capsule endoscope image.

It is still another object of the present invention, in an embodiment, to provide a computer-readable storage medium for storing a computer program. The computer program is executed by the processor to implement the steps of the three-dimensional reconstruction method of a capsule endoscope image.

Compared with the prior art, the beneficial effects of the present invention are: the three-dimensional reconstruction method of the capsule endoscope images, the electronic device and the readable storage medium of the present invention, a combination of two algorithms to obtain the image depth information values is used to improve the calculation accuracy of the image depth information values, and thus to increase the image three-dimensional reconstruction rate and improve the image identification precision.

DETAILED DESCRIPTION

The present invention can be described in detail below with reference to accompanying drawings and preferred embodiments. However, the embodiments are not intended to limit the present invention, and the structural, method, or functional changes made by those skilled in the art in accordance with the embodiments are included in the scope of the present invention.

Figure 1:
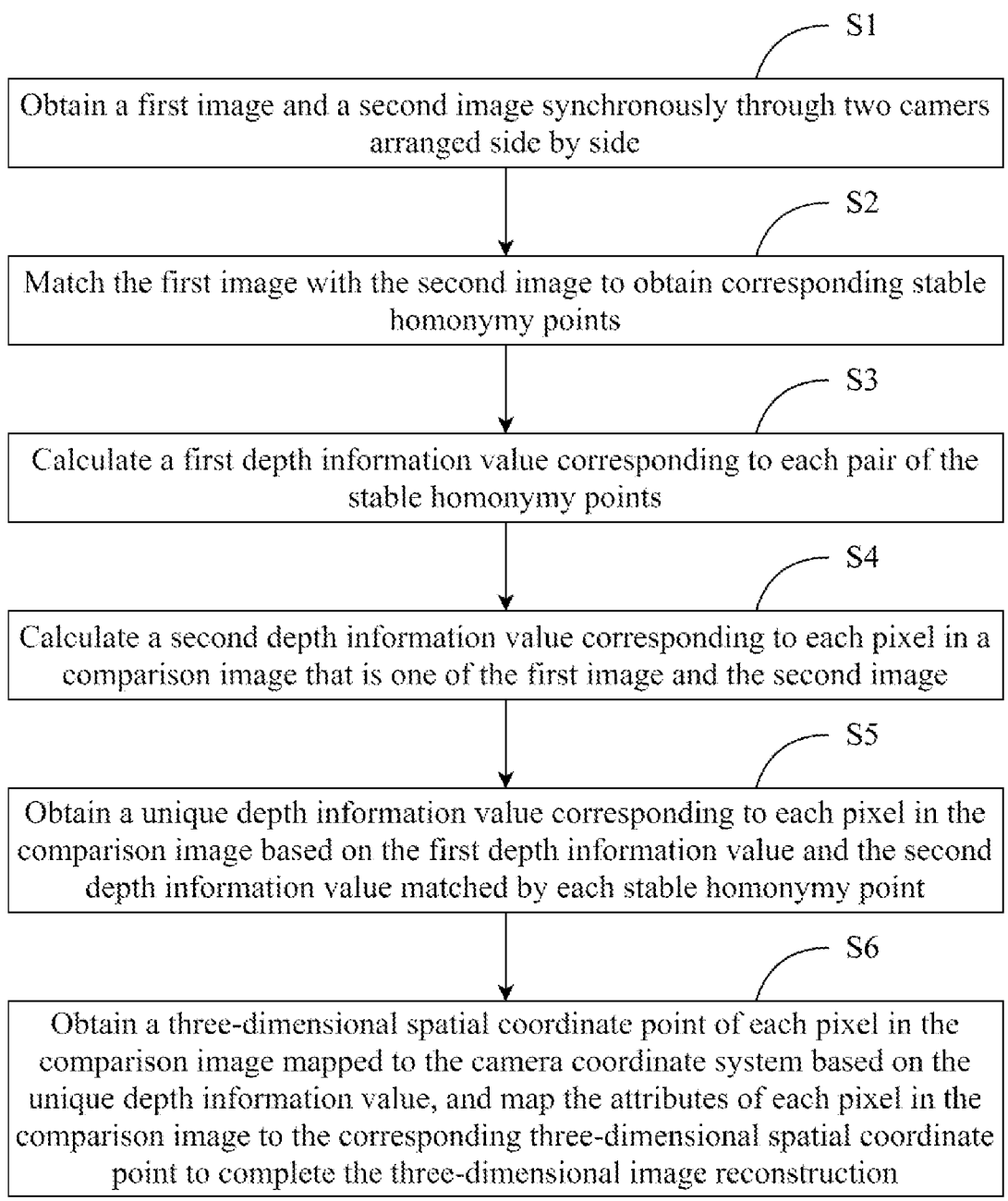
FIG. 1 is a schematic flowchart of a three-dimensional reconstruction method of capsule endoscope images in accordance with a first embodiment of the present invention.

Referring to FIG. 1, a three-dimensional reconstruction method of capsule endoscopic images is provided in a first embodiment of the present invention, the method comprising:

- step S1, obtaining a first image and a second image synchronously through two cameras arranged side by side;
- step S2, matching the first image with the second image to obtain corresponding stable homonymy points, the stable homonymy points are two pixels with a unique matching relationship in the first image and the second image after being processed by the same rule;
- step S3, calculating a first depth information value corresponding to each pair of the stable homonymy points;
- step S4, calculating a second depth information value corresponding to each pixel in a comparison image that is one of the first image and the second image;
- step S5, obtaining a unique depth information value corresponding to each pixel in the comparison image based on the first depth information value and the second depth information value matched by each stable homonymy point; and
- step S6, obtaining a three-dimensional spatial coordinate point of each pixel in the comparison image mapped to a camera coordinate system based on the unique depth information value, and mapping the attributes of each pixel in the comparison image to the corresponding three-dimensional spatial coordinate point to complete the three-dimensional image reconstruction.

For ease of description, steps S1-S6 are numbered in the above description. However, it should be noted that in the above steps, the order of steps S2-S4 can be adjusted, as long as it is ensured that they are completed between step S1 and step S5. The change of the order cannot affect the technical effects of the present invention.

For step S1, a binocular system is used in the capsule endoscope to capture images, and the binocular system comprises two sets of cameras arranged in the capsule. Typically, the two cameras have the same hardware setup parameters. Further, the two cameras arranged on the left and right synchronously capture two images, which are the first image and the second image.

Preferably, before capturing images, the two cameras are calibrated to obtain a baseline distance B between them and a focal length value f of the cameras relative to the imaging plane. It should be noted that in the specific embodiments of the present invention, the two cameras are symmetrically and parallelly arranged, and have the same focal length value between the two respectively and the imaging plane, both denoted as f.

In a specific example of the present invention, Zhang's calibration method can be used to calibrate the left and right cameras of the binocular vision system respectively, and obtain the internal and external parameter matrices cam of the two cameras, respectively. Further, the internal and external parameter matrix cam is used to correct the images captured by the corresponding camera, in order to eliminate the influence of distortion.

In other embodiments of the present invention, Zhang's calibration method is not the only camera calibration method, and a suitable camera calibration method can be selected according to the specific embodiments.

Accordingly, in step S2 and the following steps, the calculation can be performed based on the corrected first image and second image, or the calculation can be performed based on the originally obtained first image and second image, without further elaboration here.

For step S2, in the prior art, there are a plurality of methods to match the first image with the second image to obtain the corresponding stable homonymy points. For example: region-based matching methods and feature-based matching methods; specifically, feature-based matching methods such as SIFT (Scale Invariant Feature Transform), SURF (Speeded Up Robust Features), Harris corner detection operator, and others.

In a preferred embodiment of the present invention, the method disclosed in the previous patent application (Chinese Patent Application Number: 202010330852.2, title: Method for stitching images of capsule endoscope, electronic device and readable storage medium) is adopted to obtain the stable homonymy points. That is, a non-rigid dense matching method is used to detect feature points, and the detected feature points are used as the stable homonymy points.

Accordingly, for the matched first image and second image, a plurality of groups of stable homonymy points are obtained.

For step S3, in the specific embodiments of the present invention, the distance information of the camera relative to a target object, that is, the first depth information value of the present invention, can be directly calculated through the parallax between the two cameras.

Specifically, step S3 specifically includes: obtaining the baseline distance B between the two cameras, the focal length value f of the cameras relative to the imaging plane, and the coordinate values (xm1, ym1) and (xn1, yn1) of two pixels with a unique matching relationship in each stable homologous points in the corresponding image.

The first depth information value depth (xm1, ym1) is represented as: depth $$(xm1, ym1) = \frac{B \times f}{|xm1 - xn1|}.$$

Accordingly, since there are a plurality of groups of stable homonymy points, for the matched first image and second image, the first depth information values formed are multiple. In a specific example of the present invention, all stable homonymy points can be represented as an array, denoted as: depth_N, the dimension of depth_N is (N*1), where each value represents the first depth information value of each stable homonymy point. To describe this one-to-one correspondence, a stable homonymy point position information is introduced, forming a new array Dp_N=[X, Y, depth_N], with the dimension (N*3), and each row consists of the coordinate information (X, Y) representing the position and its first depth information value.

Here, each coordinate information (X, Y) can specifically express three meanings, specifically, represents the coordinate value (xm1, ym1) of the first image, or the coordinate value (xn1, yn1) of the second image, or the two coordinates ((xm1, ym1), (xn1, yn1)) of the first image and the second image.

For step S4, one of the first image and the second image is used as a comparison image, the present invention takes the first image as the comparison image as an example for a detailed introduction. Similarly, using the second image as the comparison image, the final result is the same as the result of using the first image as the comparison image, so no further examples are provided.

Specifically, various methods can also be used to obtain the depth information value of an image, which is the second depth information value of the comparison image in the present invention. For example: SFS (shape-from-shading) etc.

The SFS method can estimate the depth information values of all pixels through the grayscale image. The comparison image can be directly grayscale transformed into a grayscale image, and the depth information value obtained by the SFS method is the second depth information value in the present application. The specific implementation process is existing technology, and details are not described here. In a preferred embodiment of the present invention, a method disclosed in a previous patent application (Chinese Patent Application Number: 201910347966.5, title: Method for measuring objects in digestive tract based on imaging system) is used to obtain the second depth information value corresponding to each pixel in the comparison image.

Specifically, according to the formula z(x,y)=g($\bar{k}$ *img(x, y)) in the previous patent application, the depth image z(x,y) is calculated, and the specific value of each pixel of the z(x,y) is the second depth information value of the present application.

Here, img(x,y) is a grayscale image obtained by grayscale conversion of the comparison image; $\bar{k}$ is mean value of the correction factor in the previous patent, and in this embodiment, an empirical value is used. In addition, Table 1 in the specification of the cited patent also provides a selection method for the correction factor k; g( ) is an illumination estimation model, which is a universally applicable illumination estimation model for gastrointestinal images obtained through manual calibration. In specific applications, the comparison image of the present invention can also be used.

Accordingly, the second depth information values corresponding to all pixels in the comparison image are represented by a (S*1)-dimensional array depth_S.

For step S5, matching the first depth information value and the second depth information value corresponding to each other with the coordinate values of the pixels in the comparison image corresponding to each stable homonymy point. Specifically, obtaining the corresponding pixels in the comparison image based on the stable homonymy points, and matching the obtained first depth information value and second depth information value corresponding to the pixels in the image as a group, and matching to the current pixel. In the implementation process, finding N overlapping pixels between depth_S and depth_N by comparing coordinates, and representing all matched pixels as a (N*1)-dimensional array depth_S1.

Further, obtaining a unique depth information value corresponding to each pixel in the comparison image by combining the mutually matched first depth information value and second depth information value.

Figure 2:
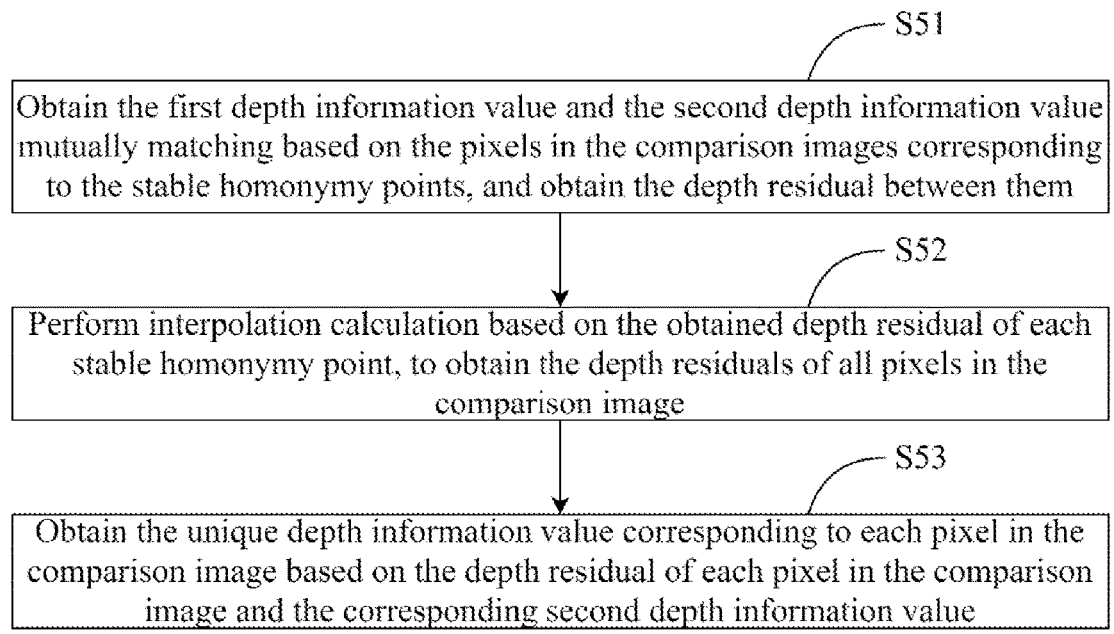
FIG. 2 is a schematic flowchart of a preferred implementation of one of steps in FIG. 1.

Specifically, referring to FIG. 2, obtaining the unique depth information value corresponding to each pixel in the comparison image comprises: step S51, obtaining the first depth information value and the second depth information value mutually matching based on the pixels in the comparison images corresponding to the stable homonymy points, and obtaining the depth residual between the first depth information value and the second depth information value;

then, d(xm1, ym1)=|depth (xm1, ym1)−depth (xm2, ym2) |;

where, (xm1, ym1) represents the pixel coordinate value in the comparison image corresponding to any stable homonymy point; d(xm1, ym1) represents the depth residual corresponding to the stable homonymy point with the coordinate value (xm1, ym1) in the comparison image, depth (xm1, ym1) represents the first depth information value corresponding to the stable homonymy point with the coordinate value (xm1, ym1) in the comparison image, and depth (xm2, ym2) represents the second depth information value corresponding to the stable homonymy point with coordinate value (xm1, ym1) in the comparison image.

Step S52, performing interpolation calculation based on the obtained depth residual of each stable homonymy point, to obtain the depth residuals of all pixels in the comparison image.

Step S53, obtaining the unique depth information value corresponding to each pixel in the comparison image based on the depth residual of each pixel in the comparison image and the corresponding second depth information value;

then, Z(xm, ym)=depth (xm, ym)+d(xm, ym);

where, (xm, ym) represents the coordinate value of any pixel in the comparison image; d(xm, ym) represents the depth residual corresponding to the pixel with the coordinate value (xm, ym) in the comparison image, depth (xm, ym) represents the second depth information value corresponding to the pixel with the coordinate value (xm, ym) in the comparison image, and Z(xm, ym) represents the unique depth information value corresponding to the pixel with the coordinate value (xm, ym) in the comparison image.

For step S52, performing interpolation calculation based on the obtained depth residual of each obtained stable homonymy point. In practical applications, in the process of calculating the second depth information value for each pixel, due to the use of illumination information to estimate the second depth information value, errors may occur during the calculation process due to factors such as overexposure and reflection, resulting in abnormal points. Therefore, performing step S51' between steps S51 and S52 to filter out obvious abnormal points by using outlier analysis method.

Specifically, the step S51' comprises: step M1, traversing the obtained depth residual d(xm1, ym1) and performing outlier analysis on it with the same parameter value to filter out obvious abnormal points.

If the traversed depth residual value d(xm1, ym1) satisfies the formula $$\frac{d(xm1, ym1) - \mu_d}{\sigma_d} > T,$$

mark the stable homonymy point corresponding to the traversed depth residual value d(xm1, ym1) as an outlier and eliminate it.

where, $\mu_d$ represents a mean value of the depth residuals corresponding to all stable homonymy points, $\sigma_d$ represents a variance of the depth residuals corresponding to all stable homonymy points, and T is a constant.

Step M2, performing interpolation calculation based on the depth residuals corresponding to the remaining stable homonymy points after the elimination is completed, that is, proceeding to step S52.

For step M1, in the specific embodiments of the present invention, set $T \in [2,4]$.

In a preferred embodiment of the present invention, for step M1 in step S51', different loop strategies can be adopted based on the specific requirements for accuracy and computational speed in the implementation. That is, step M1 can be executed once or multiple times; the more times it is executed, the more complex the calculation and the more accurate the result.

In a preferred embodiment of the present invention, after completing a single traversal for step M1, the method also includes:

obtaining the total number a of the stable homonymy points before traversing, and the total number b of the stable homonymy points after traversing and elimination; determining whether a is equal to b. If a is equal to b, proceeding to step M2; if a is not equal to b, taking the new stable homonymy points formed after elimination as the base data, and repeatedly perform step M1 until a is equal to b.

For step S52, when the depth residuals of some pixels in the comparison image are known, various interpolation methods can be used to obtain the depth residuals of other pixels in the comparison image. In a preferred embodiment of the present invention, an Inverse Distance Weighted (IDW) algorithm is used for interpolation in step S52.

Figure 3:
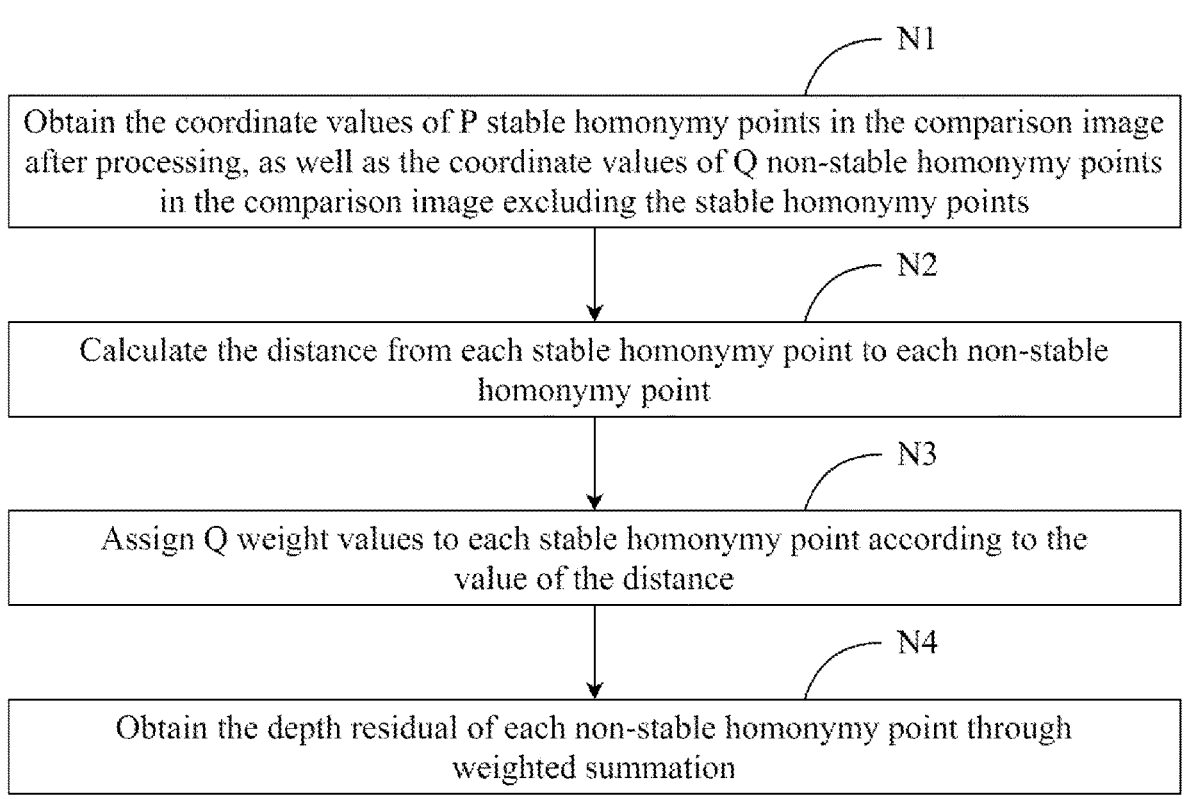
FIG. 3 is a schematic flowchart of a preferred implementation of one of steps in FIG. 2.
Figure 4:
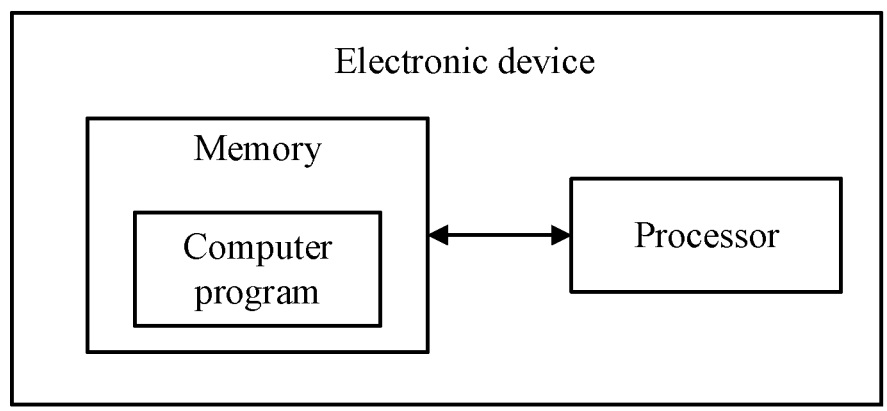
FIG. 4 is a schematic diagram of components of an exemplary electronic device in accordance with the present invention.

Specifically, referring to FIG. 3, the step S52 specifically comprises: step N1, obtaining the coordinate values $(x_i, y_i)$ of P stable homonymy points in the comparison image after processing, as well as the coordinate values $(x_j, y_j)$ of Q non-stable homonymy points in the comparison image excluding the stable homonymy points, where the total number of pixels in the comparison image is P+Q; where i=1, 2 ... P; j=1, 2 ... Q;

step N2, calculating the distance $Dist_i(j)$ from each stable homonymy point to each non-stable homonymy point;

step N3, assigning Q weight values $W_i(j)$ to each stable homonymy point $(x_i, y_i)$ according to the value of $Dist_i(j)$;

step N4, obtaining the depth residual d (j) of each non-stable homonymy point through weighted summation.

Accordingly, $Dist_i(j) = \sqrt{(x_i - x_j)^2 + (y_i - y_j)^2}$, $$W_i(j) = \frac{1}{Dist_i(j) + e},$$

$$d(j) = \sum_{i=1}^{P} d(i) * W_i(j);$$

where, d(i) represents the depth residual of the stable homonymy point with serial number i, $W_i(j)$ represents the weight value for the stable homonymy point with serial number i corresponding to the non-stable homonymy point with serial number j, $Dist_i(j)$ represents the distance between the stable homonymy point with serial number i and the non-stable homonymy point with serial number j, e is a constant value that prevents the denominator from being 0.

Preferably, set $e \in [10^{-2}, 10^{-6}]$.

Preferably, after the step S52, to eliminate local noise, the method further comprises: filtering the depth residual corresponding to each pixel in the comparison image.

In one embodiment of the present invention, median filtering is used as a filtering operator, and the depth residual of each pixel in the comparison image is set to the median depth residual of all pixels in a certain neighborhood window of that point. Further, for step S53, the filtered depth residual can be used as the basis for calculating the unique depth information value, without further elaboration.

For step S6, representing the two-dimensional coordinate value of any pixel in the comparison image as (xm, ym), and representing the three-dimensional spatial coordinate of the three-dimensional spatial coordinate point formed by mapping the two-dimensional pixel (xm, ym) as (Xm, Ym, Zm).

Using the optical center of a camera for obtaining the comparison image as the origin of the three-dimensional coordinate system, the mapping relationship between three-dimensional coordinate points and two-dimensional coordinate points can be obtained through the principle of similar triangles;

that is: $Xm = \frac{f}{(xm - xo)} B,$ $Ym = \frac{f}{(ym - yo)} B,$ where, B represents the baseline distance between two cameras, f represents the focal length value of the cameras relative to the imaging plane, (xo, yo) represents the mapping point coordinate value of the optical center of the camera forming the comparison image on the imaging plane, and the value of Zm is the unique depth information value corresponding to the two-dimensional coordinates (xm, ym).

Through coordinate transformation and the unique depth information value corresponding to each pixel in the comparison image, a three-dimensional model can be reconstructed.

Further, the initial three-dimensional model's coordinates only contain a single hue. To make it more realistic, texture mapping can be applied to the three-dimensional model.

Specifically, based on the correspondence between three-dimensional spatial coordinates and the pixels in a two-dimensional comparison image, the color and texture information contained in the comparison image is mapped or overlaid onto the surface of the reconstructed three-dimensional model. Specifically, assigning the color values of the image directly to the corresponding three-dimensional spatial points and smoothing them to complete the three-dimensional image reconstruction.

In a specific example of the present invention, a three-dimensional reconstruction method of the capsule endoscope image is used for simulating gastric experiments. In the measurement of specific lesions, the error under a 6 mm baseline is 3.97%.

Further, an embodiment of the present invention provides an electronic device, comprising a memory and a processor. The memory stores a computer program that can run on the processor, and the processor executes the computer program to implement the steps of the three-dimensional reconstruction method of the capsule endoscope image.

Further, an embodiment of the present invention provides a computer-readable storage medium for storing a computer program. The computer program is executed by the processor to implement the steps of the three-dimensional reconstruction method of the capsule endoscope image.

In summary, the three-dimensional reconstruction method of the capsule endoscope image, the electronic device and the readable storage medium of the present invention, a combination of two algorithms to obtain the image depth information values is used to improve the calculation accuracy of the image depth information values, and thus to increase the image three-dimensional reconstruction rate and improve the image identification precision.

For the convenience of description, the device is described in various modules divided by functions separately. When implementing the present invention, the functions of the various modules can be implemented in the same or different software and/or hardware.

The device implementations described above are merely illustrative. The modules described as separate components may or may not be physically separated, and the components displayed as modules may or may not be physical modules, that is, they may be located in one place, or may also be distributed over a plurality of network modules. Some or all of the modules may be selected according to actual needs to achieve the object of the embodiment. It can be understood and implemented by ordinary persons skilled in the art without creative work.

It should be understood that, although the specification is described in terms of embodiments, not every embodiment merely comprises an independent technical solution. Those skilled in the art should have the specification as a whole, and the technical solutions in each embodiment may also be combined as appropriate to form other embodiments that can be understood by those skilled in the art.

The series of detailed descriptions listed above are only specific descriptions for the feasible embodiments of the present invention, and they are not used to limit the protection scope of the present invention. Changes should all be included within the protection scope of the present invention.

The invention claimed is:

1. A three-dimensional reconstruction method of a capsule endoscope image, comprising:
    obtaining a first image and a second image synchronously through two cameras arranged side by side;
    matching the first image with the second image to obtain corresponding stable homonymy points, wherein the stable homonymy points are two pixels with a unique matching relationship in the first image and the second image after being processed by the same rule;
    calculating a first depth information value corresponding to each pair of the stable homonymy points;
    calculating a second depth information value corresponding to each pixel in a comparison image that is one of the first image and the second image;
    obtaining a unique depth information value corresponding to each pixel in the comparison image based on the first depth information value and the second depth information value matched by each stable homonymy point; and
    obtaining a three-dimensional spatial coordinate point of each pixel in the comparison image mapped to the camera coordinate system based on the unique depth information value, and mapping the attributes of each pixel in the comparison image to the corresponding three-dimensional spatial coordinate point to complete the three-dimensional image reconstruction,
    wherein obtaining the unique depth information value corresponding to each pixel in the comparison image based on the first depth information value and the second depth information value matched by each stable homonymy point comprises:
    obtaining the first depth information value and the second depth information value mutually matching based on the pixels in the comparison images corresponding to the stable homonymy points, and obtaining a depth residual between the first depth information value and the second depth information value;
    then, $d(xm1, ym1) = |depth(xm1, ym1) - depth(xm2, ym2)|$;
    wherein, $(xm1, ym1)$ represents a pixel coordinate value in the comparison image corresponding to any stable homonymy point; $d(xm1, ym1)$ represents the depth residual corresponding to the stable homonymy point with the coordinate value $(xm1, ym1)$ in the comparison image, $depth(xm1, ym1)$ represents the first depth information value corresponding to the stable homonymy point with the coordinate value $(xm1, ym1)$ in the comparison image, and $depth(xm2, ym2)$ represents the second depth information value corresponding to the stable homonymy point with the coordinate value $(xm1, ym1)$ in the comparison image;
    performing interpolation calculation based on the obtained depth residual of each stable homonymy point, to obtain the depth residuals of all pixels in the comparison image;
    obtaining the unique depth information value corresponding to each pixel in the comparison image based on the depth residual of each pixel in the comparison image and the corresponding second depth information value;
    then, $Z(xm, ym) = depth(xm, ym) + d(xm, ym)$;
    wherein, $(xm, ym)$ represents the coordinate value of any pixel in the comparison image; $d(xm, ym)$ represents the depth residual corresponding to the pixel with the coordinate value $(xm, ym)$ in the comparison image; $depth(xm, ym)$ represents the secondary depth information value corresponding to the pixel with the coordinate value $(xm, ym)$ in the comparison image; and
    $Z(xm, ym)$ represents the unique depth information value corresponding to the pixel with the coordinate value $(xm, ym)$ in the comparison image.

2. The three-dimensional reconstruction method of claim 1, wherein matching the first image with the second image to obtain corresponding stable homonymy points comprises:
- detecting feature points using a non-rigid dense matching method, and the detected feature points are used as the stable homonymy points.

3. The three-dimensional reconstruction method of claim 1, wherein calculating the first depth information value corresponding to each pair of the stable homonymy points comprises:
- obtaining a baseline distance B between two cameras, a focal length value f of the cameras relative to the imaging plane, and coordinate values (xm1, ym1) and (xn1, yn1) of the two pixels with a unique matching relationship in each stable homologous points in the corresponding image;
- the first depth information value depth (xm1, ym1) is represented as:

$$\text{depth}(xm1, ym1) = \frac{B \times f}{|xm1 - xn1|}.$$

4. The three-dimensional reconstruction method of claim 1, wherein before performing interpolation calculation based on the obtained depth residual of each stable homonymy point, the method specifically comprises:
- M1, traversing the obtained depth residual d(xm1, ym1) and performing outlier analysis on it with the same parameter value to filter out obvious abnormal points;
- marking the stable homonymy point corresponding to the traversed depth residual value d(xm1, ym1) as an outlier and eliminating it when the traversed depth residual value d(xm1, ym1) satisfies the formula $$\frac{d(xm1, ym1) - \mu_d}{\sigma_d} > T;$$

wherein, $\mu_d$ represents a mean value of the depth residuals corresponding to all stable homonymy points, $\sigma_d$ represents a variance of the depth residuals corresponding to all stable homonymy points, and T is a constant;
- M2, performing interpolation calculation based on the depth residuals corresponding to the remaining stable homonymy points after the elimination is completed.

5. The three-dimensional reconstruction method of claim 4, wherein after one traversing is completed in step M1, the method also comprises:
- obtaining the total number a of the stable homonymy points before traversing, and the total number b of the stable homonymy points after traversing and elimination;
- determining whether a is equal to b;
- if a is equal to b, proceeding to step M2;
- if a is not equal to b, taking the new stable homonymy points formed after elimination as the base data, and repeatedly perform step M1 until a equals b.

6. The three-dimensional reconstruction method of claim 1, wherein performing interpolation calculation based on the obtained depth residual of each obtained stable homonymy point comprises:
- obtaining the coordinate values $(x_i, y_i)$ of P stable homonymy points in the comparison image after processing, as well as the coordinate values $(x_j, y_j)$ of Q non-stable homonymy points in the comparison image excluding the stable homonymy points, wherein the total number of pixels in the comparison image is P+Q; wherein i=1, 2 ... P; j=1, 2 ... Q;
- calculating the distance $\text{Dist}_i(j)$ from each stable homonymy point to each non-stable homonymy point;
- assigning Q weight values $W_i(j)$ to each stable homonymy point $(x_i, y_i)$ according to the value of $\text{Dist}_i(j)$;
- obtaining the depth residuals d(j) of each non-stable homonymy point through weighted summation:

$$\text{Dist}_i(j) = \sqrt{(x_i - x_j)^2 + (y_i - y_j)^2},$$

$$W_i(j) = \frac{1}{\text{Dist}_i(j) + e},$$

$$d(j) = \sum_{i=1}^{P} d(i) * W_i(j);$$

wherein, d(i) represents the depth residual of the stable homonymy point with serial number i, $W_i(j)$ represents the weight value for the stable homonymy point with serial number i corresponding to the non-stable homonymy point with serial number j; e is a constant value that prevents the denominator from being 0.

7. A three-dimensional reconstruction method of claim 1, wherein obtaining the three-dimensional spatial coordinate point of each pixel in the comparison image mapped to the camera coordinate system based on the unique depth information value comprises:
- representing a two-dimensional coordinate value of any pixel in the comparison image as (xm, ym), and representing the three-dimensional spatial coordinate of the three-dimensional spatial coordinate point formed by mapping the two-dimensional pixel (xm, ym) as (Xm, Ym, Zm):

$$Xm = \frac{f}{(xm - xo)}B,$$

$$Ym = \frac{f}{(ym - yo)}B,$$

wherein, B represents a baseline distance between two cameras, f represents a focal length value of the cameras relative to the imaging plane, (xo, yo) represents the mapping point coordinate value of an optical center of the camera forming the comparison image on the imaging plane, and the value of Zm is the unique depth information value corresponding to the two-dimensional coordinate (xm, ym).

8. An electronic device, comprising a memory and a processor, wherein the memory stores a computer program that runs on the processor, and the processor executes the program to implement steps of a three-dimensional reconstruction method of a capsule endoscope image, wherein the method comprises:
- obtaining a first image and a second image synchronously through two cameras arranged side by side;
- matching the first image with the second image to obtain corresponding stable homonymy points, wherein the stable homonymy points are two pixels with a unique matching relationship in the first image and the second image after being processed by the same rule;
- calculating a first depth information value corresponding to each pair of the stable homonymy points;

calculating a second depth information value corresponding to each pixel in a comparison image that is one of the first image and the second image;
obtaining a unique depth information value corresponding to each pixel in the comparison image based on the first depth information value and the second depth information value matched by each stable homonymy point; and
obtaining a three-dimensional spatial coordinate point of each pixel in the comparison image mapped to the camera coordinate system based on the unique depth information value, and mapping the attributes of each pixel in the comparison image to the corresponding three-dimensional spatial coordinate point to complete the three-dimensional image reconstruction, wherein obtaining the unique depth information value corresponding to each pixel in the comparison image based on the first depth information value and the second depth information value matched by each stable homonymy point comprises:
obtaining the first depth information value and the second depth information value mutually matching based on the pixels in the comparison images corresponding to the stable homonymy points, and obtaining a depth residual between the first depth information value and the second depth information value;
then, d(xm1, ym1)=|depth (xm1, ym1)−depth (xm2, ym2)|;
wherein, (xm1, ym1) represents a pixel coordinate value in the comparison image corresponding to any stable homonymy point; d(xm1, ym1) represents the depth residual corresponding to the stable homonymy point with the coordinate value (xm1, ym1) in the comparison image, depth (xm1, ym1) represents the first depth information value corresponding to the stable homonymy point with the coordinate value (xm1, ym1) in the comparison image, and depth (xm2, ym2) represents the second depth information value corresponding to the stable homonymy point with the coordinate value (xm1, ym1) in the comparison image;
performing interpolation calculation based on the obtained depth residual of each stable homonymy point, to obtain the depth residuals of all pixels in the comparison image;
obtaining the unique depth information value corresponding to each pixel in the comparison image based on the depth residual of each pixel in the comparison image and the corresponding second depth information value;
then, Z(xm, ym)=depth (xm, ym)+d(xm, ym);
wherein, (xm, ym) represents the coordinate value of any pixel in the comparison image; d(xm, ym) represents the depth residual corresponding to the pixel with the coordinate value (xm, ym) in the comparison image; depth (xm, ym) represents the secondary depth information value corresponding to the pixel with the coordinate value (xm, ym) in the comparison image; and Z(xm, ym) represents the unique depth information value corresponding to the pixel with the coordinate value (xm, ym) in the comparison image.

9. A computer-readable storage medium having stored thereon a computer program that, when executed by a processor, implements steps of a three-dimensional reconstruction method of a capsule endoscope image, wherein the method comprises:
obtaining a first image and a second image synchronously through two cameras arranged side by side;
matching the first image with the second image to obtain corresponding stable homonymy points, wherein the stable homonymy points are two pixels with a unique matching relationship in the first image and the second image after being processed by the same rule;
calculating a first depth information value corresponding to each pair of the stable homonymy points;
calculating a second depth information value corresponding to each pixel in a comparison image that is one of the first image and the second image;
obtaining a unique depth information value corresponding to each pixel in the comparison image based on the first depth information value and the second depth information value matched by each stable homonymy point; and
obtaining a three-dimensional spatial coordinate point of each pixel in the comparison image mapped to the camera coordinate system based on the unique depth information value, and mapping the attributes of each pixel in the comparison image to the corresponding three-dimensional spatial coordinate point to complete the three-dimensional image reconstruction,
wherein obtaining the unique depth information value corresponding to each pixel in the comparison image based on the first depth information value and the second depth information value matched by each stable homonymy point comprises:
obtaining the first depth information value and the second depth information value mutually matching based on the pixels in the comparison images corresponding to the stable homonymy points, and obtaining a depth residual between the first depth information value and the second depth information value;
then, d(xm1, ym1)=|depth (xm1, ym1)−depth (xm2, ym2)|;
wherein, (xm1, ym1) represents a pixel coordinate value in the comparison image corresponding to any stable homonymy point; d(xm1, ym1) represents the depth residual corresponding to the stable homonymy point with the coordinate value (xm1, ym1) in the comparison image, depth (xm1, ym1) represents the first depth information value corresponding to the stable homonymy point with the coordinate value (xm1, ym1) in the comparison image, and depth (xm2, ym2) represents the second depth information value corresponding to the stable homonymy point with the coordinate value (xm1, ym1) in the comparison image;
performing interpolation calculation based on the obtained depth residual of each stable homonymy point, to obtain the depth residuals of all pixels in the comparison image;
obtaining the unique depth information value corresponding to each pixel in the comparison image based on the depth residual of each pixel in the comparison image and the corresponding second depth information value;
then, Z(xm, ym)=depth (xm, ym)+d(xm, ym);
wherein, (xm, ym) represents the coordinate value of any pixel in the comparison image; d(xm, ym) represents the depth residual corresponding to the pixel with the coordinate value (xm, ym) in the comparison image; depth (xm, ym) represents the secondary depth information value corresponding to the pixel with the coordinate value (xm, ym) in the comparison image; and Z(xm, ym) represents the unique depth information value corresponding to the pixel with the coordinate value (xm, ym) in the comparison image.

* * * * *